United States Patent
Hoffmann et al.

(10) Patent No.: US 8,167,850 B2
(45) Date of Patent: May 1, 2012

(54) CYLINDER/PISTON UNIT WITH AT LEAST THREE SEALING ELEMENTS

(75) Inventors: Hans-Rainer Hoffmann, Neuwied (DE); Rudolf Matusch, Marburg (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 530 days.

(21) Appl. No.: 12/380,385

(22) Filed: Feb. 26, 2009

(65) Prior Publication Data
US 2009/0166978 A1 Jul. 2, 2009

Related U.S. Application Data

(63) Continuation-in-part of application No. PCT/EP2007/007609, filed on Aug. 31, 2007.

(30) Foreign Application Priority Data

Sep. 27, 2006 (DE) .......................... 10 2006 045 959

(51) Int. Cl.
*A61M 5/315* (2006.01)
(52) U.S. Cl. ........................................ 604/222; 604/218
(58) Field of Classification Search .......... 604/218–231, 604/181, 187, 232–234
See application file for complete search history.

(56) References Cited

U.S. PATENT DOCUMENTS

| | | | |
|---|---|---|---|
| 4,861,340 A | | 8/1989 | Smith et al. |
| 6,053,895 A | * | 4/2000 | Kolberg et al. ............... 604/218 |
| 2004/0138611 A1 | * | 7/2004 | Griffiths et al. ................ 604/82 |

FOREIGN PATENT DOCUMENTS

| | | |
|---|---|---|
| CA | 2 608 638 | 5/2007 |
| EP | 0001452 A1 | 4/1979 |

(Continued)

OTHER PUBLICATIONS

FR 720293; Published—Feb. 17, 1932; Country—France; Translation—No.

(Continued)

*Primary Examiner* — Kevin C Sirmons
*Assistant Examiner* — Phillip Gray
(74) *Attorney, Agent, or Firm* — R. S. Lombard; K. Bach

(57) ABSTRACT

A cylinder/piston unit is disclosed for pre-fill, storage and release when desired of an active substance, such as a medicament. The cylinder/piston unit is provided with a cylinder and with a piston which is guided therein and which is sealed off in a sterile manner by a rubber seal, the cylinder and the piston enclosing a chamber that can be filled at least temporarily with active substance, and the cylinder having at least one discharge element at its front end. For this purpose, the piston resting in a rear position is sealed off relative to the cylinder in a sterile manner by a static front sealing element and by a static rear sealing element. Arranged spatially behind each static sealing element, there is a parking area for receiving the respective sealing element. When the piston is actuated, the individual static sealing elements are transferred from their respective sealing position into a parked position located in the parking area, and each sealing element in the parked position touches only the cylinder wall or only the piston wall. With the present invention, a cylinder/piston unit is developed which can be pre-filled and in which, despite a sterile sealing of the piston, only a slight force has to be applied in order to accelerate and/or move the piston.

11 Claims, 5 Drawing Sheets

FOREIGN PATENT DOCUMENTS

| | | |
|---|---|---|
| FR | 875780 | 7/1942 |
| GB | 743789 | 1/1956 |
| GB | 1 168 201 A | 10/1969 |
| JP | 2000 342688 A | 12/2000 |
| WO | WO 88/05315 A | 7/1988 |
| WO | WO 99/44659 A | 9/1999 |

OTHER PUBLICATIONS

JP 08-238316 Abstract; Published—Sep. 17, 1996; Country—Japan; Translation—No.

* cited by examiner

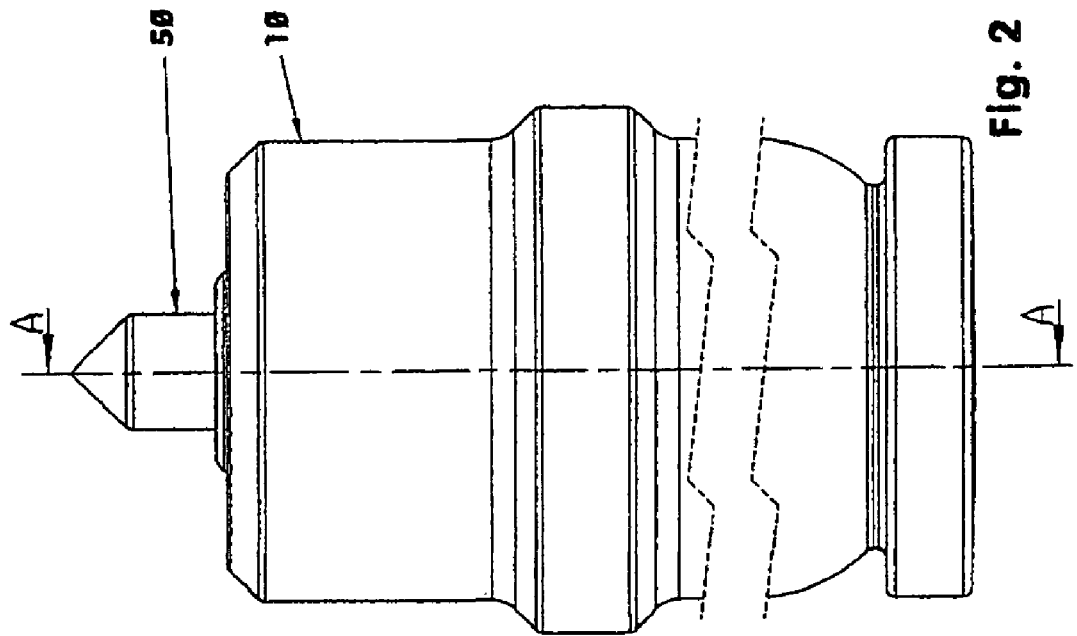
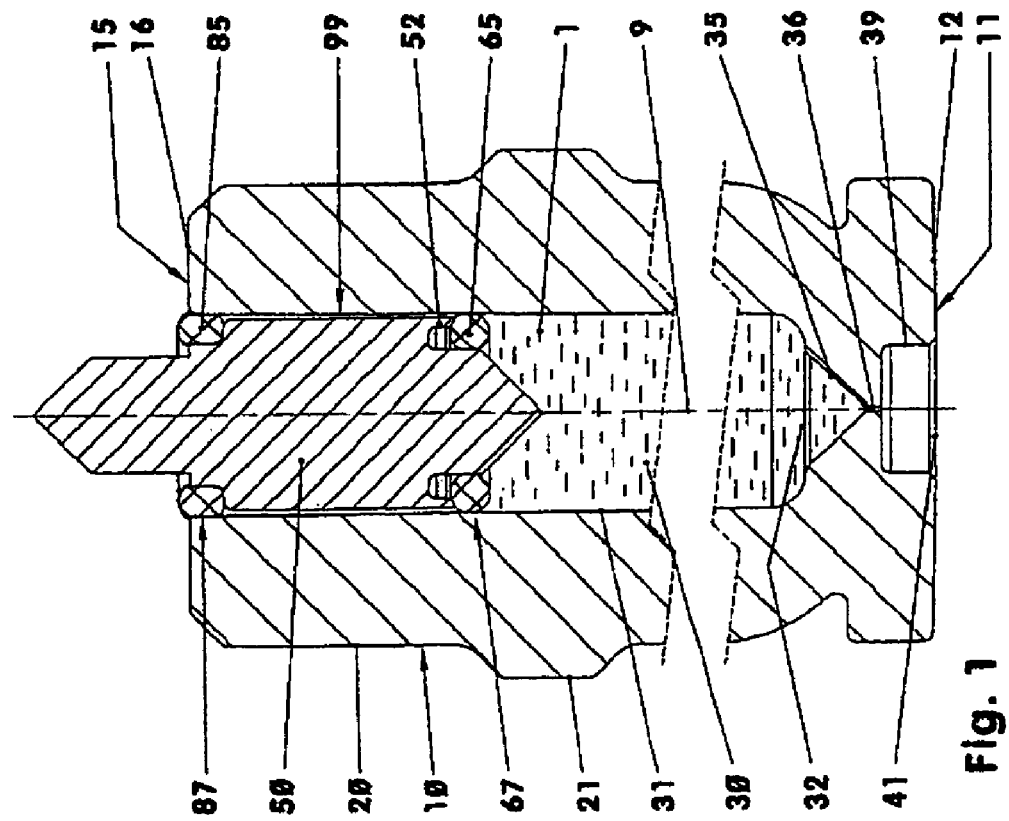
Fig. 1
Fig. 2

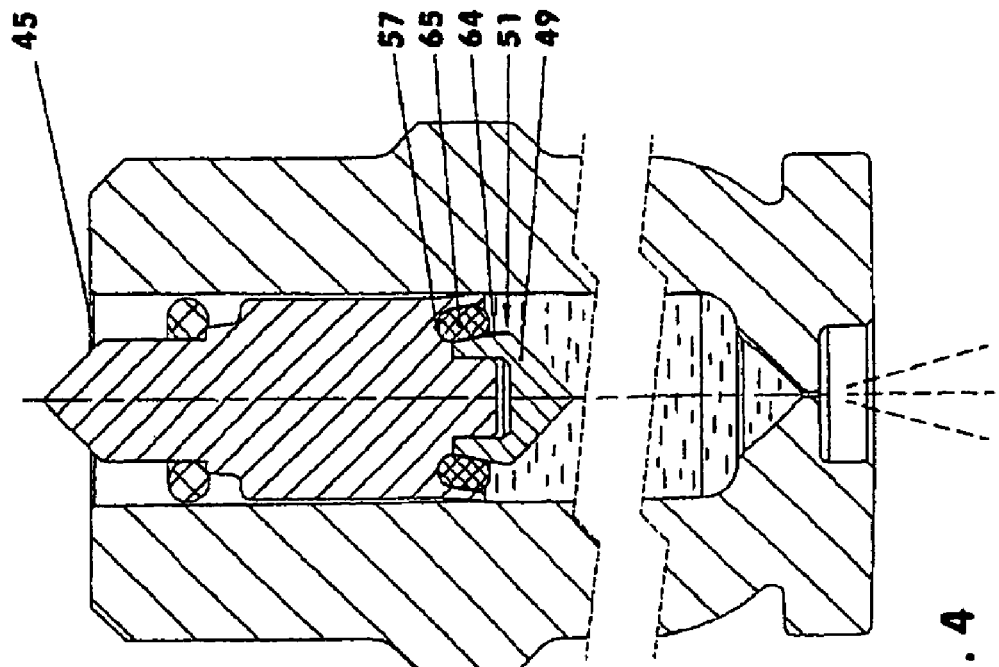
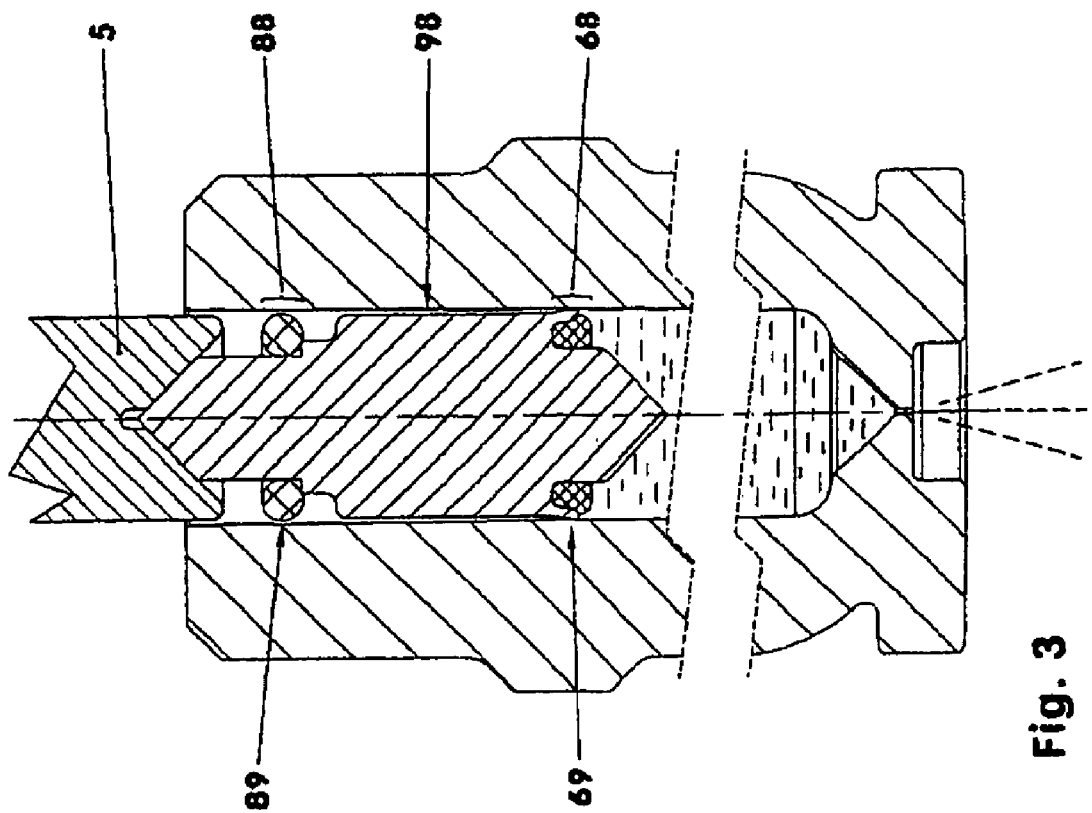

CYLINDER/PISTON UNIT WITH AT LEAST THREE SEALING ELEMENTS

CROSS-REFERENCE TO RELATED APPLICATION

This is a continuation-in-part application of pending international application PCT/EP 2007/007609 filed Aug. 31, 2007 and claiming the priority of German Application No. 10 2006 045 959.8 filed Sep. 27, 2006.

BACKGROUND OF THE INVENTION

The present invention relates to a cylinder/piston unit with a cylinder and with a piston which is guided therein and is sealed off in a sterile manner by a rubber seal, the cylinder and the piston enclosing a chamber that can be filled at least temporarily with active substance, and the cylinder having at least one discharge element at its front end.

In the case of medicament chambers or syringes that are stored in a filled state and that are closed off in a sterile manner by means of a piston among other things, the piston coming into contact with the injection solution is made of rubber or has at least a rubber seal. Since such a piston that provides sterile sealing has a high degree of static friction and kinetic friction relative to the glass cylinder or plastic cylinder, the piston according to DIN 13098, part 1, is lubricated with polydimethylsiloxane, for example. Consequently, the lubricant is also administered along with the injection solution.

Another alternative is to seal the medicament chamber or syringe barrel (see DE 10 2005 054 600). In the latter document, the pistons do not have any rubber seals. Here, for example, the rear face of a medicament chamber is heat-sealed with a film or is closed off in a sterile manner by a spray-on varnish.

The object of the present invention is therefore to develop a cylinder/piston unit which can be pre-filled and in which, despite a sterile sealing of the piston, only a slight force has to be applied in order to accelerate and/or move the piston.

SUMMARY OF THE INVENTION

The invention relates to a cylinder/piston unit with a cylinder and with a piston which is guided therein and which is sealed off in a sterile manner by a rubber seal, the cylinder and the piston enclosing a chamber that can be filled at least temporarily with active substance, and the cylinder having at least one discharge element at its front end.

The present invention provides, the piston resting in a rear position is sealed off relative to the cylinder in a sterile manner by a static front sealing element and by a static rear sealing element, both sealing elements in a sealing position each bearing on the wall of the cylinder and each on the wall of the piston. Arranged spatially behind each static sealing element, there is a parking area for receiving the respective sealing element. When the piston is actuated, the individual static sealing elements are transferred from their respective sealing position into a parked position located in the parking area, and each sealing element in the parked position touches either only the cylinder wall or only the piston wall. At least one dynamic sealing element on the piston side is arranged between the two static sealing elements and bears on the wall of the cylinder at least when the piston is actuated.

By means of the invention, a cylinder/piston unit is created which can be used, for example, in a subcutaneous injection device and in which, as a result of the structural configuration of the seals lying between the inner wall of the cylinder and the outer contour of the piston, and of their seal seats, the piston generates only a slight frictional resistance during its working movement. Moreover, the cylinder/piston unit comprises a piston which is self-sealing, in accordance with the technical principle of self help, and which, by virtue of the configuration of its sealing means among other things, sits in the cylinder free of lubricant.

In the described cylinder/piston unit, the piston is inserted into the pre-filled medicament chamber by a vacuum application process, for example. Under vacuum, the piston is in this case placed on the level of the liquid in the bore of the medicament chamber. All hollow spaces in the environment of the piston are thus under vacuum, as long as they lie in front of the rear static sealing element. The latter seals off the movement joint of the cylinder/piston unit from the environment.

If the piston is now accelerated in order to discharge the injection solution, the front sealing element is moved from its sealing position to a parked position on account of the pressure of the liquid. In doing so, this static sealing element loses its frictional contact with the cylinder. A regular, dynamic piston seal, which has only a slight kinetic friction resistance, assumes the sealing role between piston and cylinder. Because of its considerable static friction, the rear static sealing element continues to adhere to the cylinder, for example, although the piston is already moving downwards. The static friction leads to this sealing element being stripped off. It slips into a parked position, in which it is not able to impede the piston movement.

BRIEF DESCRIPTION OF THE DRAWINGS

Further details of the invention will become clear from the following illustrative embodiments depicted schematically in the drawings, where:

FIG. 1 shows a cylinder/piston unit, with a piston positioned in the upper end position;

FIG. 2 shows a side view of FIG. 1;

FIG. 3 shows a cylinder/piston unit as liquid is being ejected;

FIG. 4 shows the same view as in FIG. 3, but with another front piston portion;

DETAILED DESCRIPTION OF THE PARTICULAR EMBODIMENTS

Figure 6:
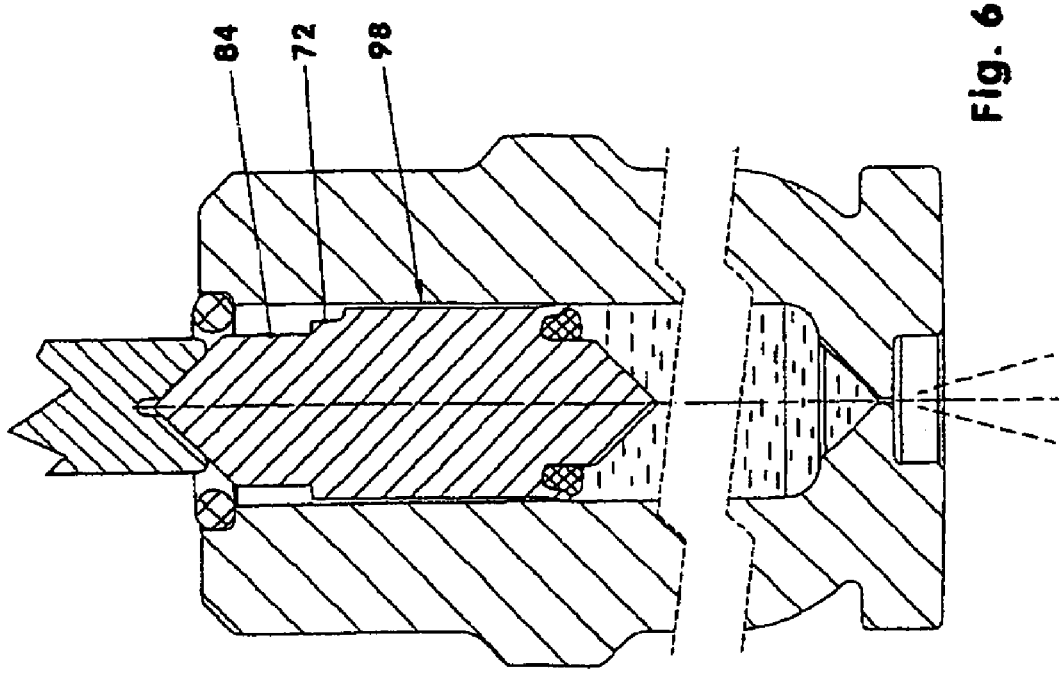
FIG. 6 shows the same view as in FIG. 5, but during ejection of liquid.

FIG. 1 shows a cylinder/piston unit as is used, for example, in a needle-less subcutaneous injection device. It comprises a cylinder (10) and a piston (50), for example without a piston rod, and with a front sealing element (65) and a rear sealing element (85) made of rubber. The cylinder (10) and the piston (50) enclose, within a chamber (30), a product (1) that is to be administered subcutaneously or a liquid carrier material, for example distilled water or physiological saline solution. The piston (50) in FIG. 1 is shown in a rear position (99). The cylinder/piston unit is, for example, designed to be used just once and then disposed of. It is used to administer a nominal volume of medicament of 0.1 to 2 ml (millilitre), for example.

If appropriate, a nominal volume of medicament of 3 ml can also be administered. The cylinder (10), designed here only by way of example without an integrated injection needle, withstands a temporary pressure load of at least $300 \times 10^5$ Pa (Pascal) during use in a subcutaneous injection device.

The cylinder (10) has roughly the shape of the syringe barrel of a standard disposable syringe. At the front end (11), there is a nozzle-like discharge element (36) which, in the front and, for example, flat end face (12) of the cylinder, terminates in what is for example a circular opening (41) of a free jet aperture (39). If appropriate, instead of the nozzle-like discharge element, an injection needle (not shown in the present figures) can be fitted.

The rear cylinder end face (16) is situated at the rear end of the cylinder (10). It is plane and is oriented perpendicular to the centre line (9) of the cylinder.

An outer contour (20) of any desired jacket surface is located between the rear end face (16) and the front end face (12). The shape of the outer contour (20) of the cylinder (10) is in most cases independent of the functional designation "cylinder (10)". The outer contour (20) can, among other things, have one or more partial flattened areas, flanges, thread sections, bayonet closure parts or the like in order to permit adaptation to an injector and, if appropriate, to prevent it from inadvertently rolling to the sides when handled on a flat support surface.

FIGS. 1 to 6 show, on the outer contour (20), a more or less centrally arranged adapter flange (21). This is used for fixing the cylinder in a dimensionally stable manner on the subcutaneous injection device (not shown). Here, a collar of the injector housing or another adapter contour engages round the corresponding flange (21) of the cylinder (10). An adapter can be dispensed with in the case of an injector design having an almost complete cylinder around the injector housing.

The external diameter of the adapter flange (21) is, for example, greater by at least one fifth of the cylinder wall thickness than the external diameter of the adjacent outer contour (20) of the cylinder (10). The flange (21) too can have one or more flattened areas about its sides in order to impede a rolling movement. Instead of the flattened areas, it is also conceivable to provide notches, grooves, beads or flutings.

FIG. 2 shows a side view of a filled cylinder (10) in which a piston (50) sealed in a sterile manner is fitted.

The inner contour of the cylinder (10) comprises the inner wall (31) of the cylinder, if appropriate with a housing collar (46), (see FIGS. 5 and 6), a cylinder base (32), an outflow funnel (35), a nozzle bore (36) and a free jet aperture (39).

According to the illustrative embodiments shown, the cylinder inner wall (31), which is smooth for example, tapers linearly from the rear forwards. According to FIG. 1 and FIGS. 3 to 6, it also extends over the entire piston stroke range. All cross sections of the inner wall (31) of the cylinder outside the area of the outflow funnel or funnels (35) are also circular. For example, the inner wall (31) of the cylinder only narrows over a piston stroke (3) of 18 millimetres from a diameter of 7 millimetres to 6 millimetres. This corresponds to a taper angle of about 3.2 degrees.

Instead of the specific cases shown here, the cross sections can also change their shape, in addition to their surface area, over the piston stroke. Thus, the inner wall of the cylinder could, for example, have an oval cross-sectional shape at its rear end, while a cross section lying nearer the front end has a round or polygonal shape. Moreover, it is also possible for the change in cross-sectional surface area along the piston stroke to be non-linear. For example, in order to reduce the piston braking action, the taper can start only in the final third of the ejection stroke. The transition between portions having different cross sections is generally constant.

The outflow funnel (35) tapers between the cylinder base (32) and the nozzle bore (36) in a linear manner, for example. The nozzle bore (36), whose diameter lies for example between 0.1 and 0.4 millimetres, is two to four times as long as its diameter. The nozzle bore (36) is adjoined by a free jet aperture (39) in the shape of a cylinder chamber. The aperture (39) has a flat base, which is additionally oriented perpendicular to the centre line of the nozzle bore (36). Its diameter corresponds to eight to sixteen times the nozzle bore diameter, if the aperture depth is at least twice as great as the nozzle bore length.

Figure 5:
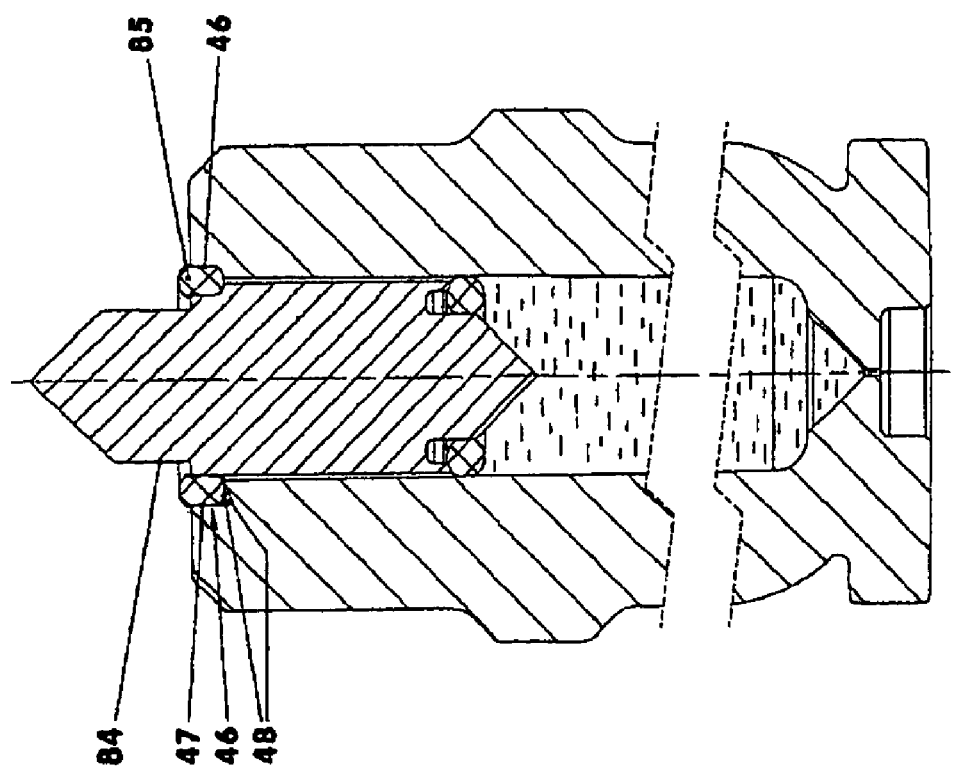
FIG. 5 shows the same view as in FIG. 1, but with other rear sealing element locations.

At the rear end (15) of the cylinder (10), the housing collar (46) is located in the transition area between the cylinder inner wall (31) and the end face (16) (see FIGS. 5 and 6). The housing collar (46) has a radial collar surface (47) and an axial collar surface (48). The rear areas of the cylinder (10) and of the piston (50) are shown asymmetrically in FIGS. 5 and 6, to dispense with the need for further drawings. The right-hand side of FIG. 5 belongs to the right-hand side of FIG. 6. Likewise, the left-hand sides of FIGS. 5 and 6 match each other alone.

On the left-hand side, the radial collar surface (47) has a greater diameter than on the right-hand side. The collar surfaces (47) are shown as cylinders only by way of example. To increase the sealing action, they can be provided with circumferential elevations or other structures, for example. The axial sealing surfaces (48) are plane. FIG. 5 also shows, in broken lines, a sealing surface (48) having the shape of a truncated cone.

Figure 8:
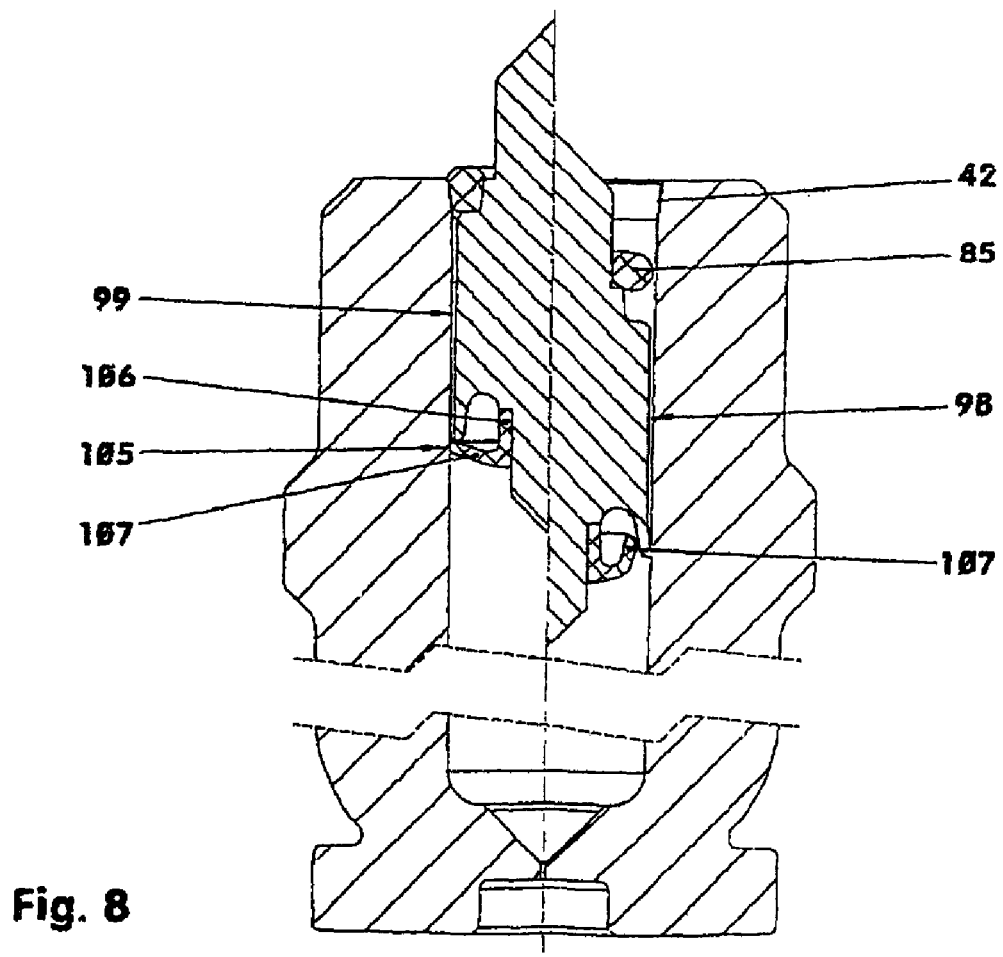
FIG. 8 shows a cylinder/piston unit with front lip seal.

If appropriate, a bevel (42), for example of 5 degrees, can be provided between the cylinder inner wall (31) and the rear end face (16) in order to permit easier fitting of the piston (10) (see FIG. 8).

The material used for the cylinder (10) is a transparent, amorphous thermoplastic, for example a copolymer based on cycloolefins and ethylenes or □-olefins (COC). Polycarbonate, for example, as sold under the registered U.S. trademark, Makrolon, by Bayer Atiengesellschaft, Leverkusen-Bayerwerk, Germany, is also suitable for cylinders (10) that are filled immediately before injection.

The piston (50) guided in the cylinder (10) must compensate for the change in cross section of the inner wall of the cylinder by having a corresponding reduction in its sealing cross section. The wall friction should increase only to an inappreciable extent in this case.

Figure 7:
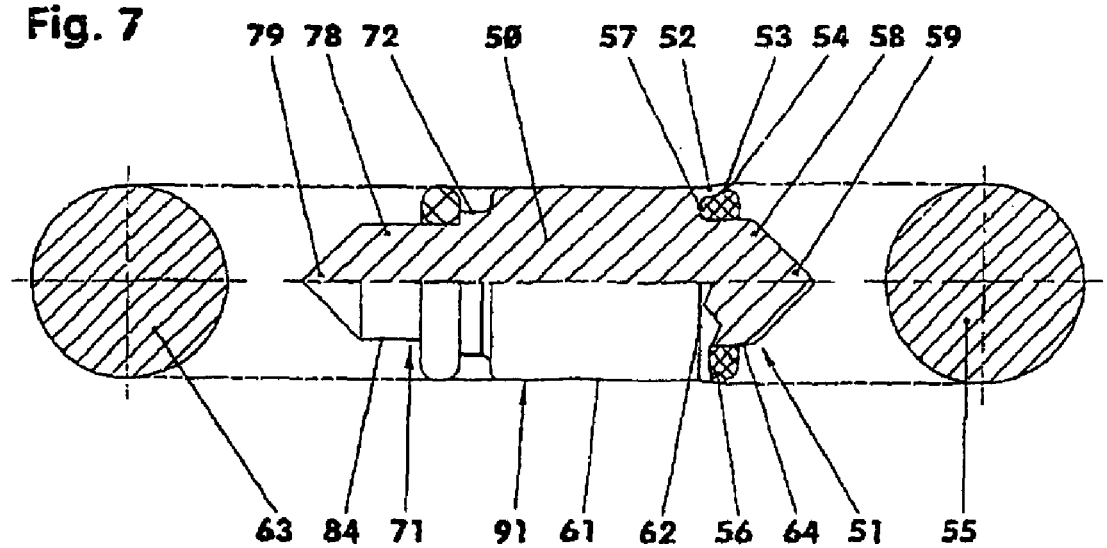
FIG. 7 shows a partial section through the actuated cylinder piston, together with cross sections.

To achieve this among other things, the piston (50) can be divided into three portions (51, 71, 91) and has, in the front portion (51), a sealing lip in the form of a skirt (52) (see FIG. 7). The portion (51) is adjoined by, in succession, the central portion (91) and the rear portion (71).

The central portion (91) has the shape of a cylinder. It fits without deformation into the entire stroke area of the chamber (30). At the front, it is adjoined centrally by a front piston core (58), which ends for example in a conical piston tip (59). The skirt (52) is situated around the core (58), and the core wall (64), shown as a cylinder in FIGS. 1, 2 and 5 to 7, protrudes past the skirt (52). According to FIG. 7, an axial annular groove (57) lies between the skirt (52) and the core (58). The diameter of the core wall (64) is chosen such that the sealing element (65) in the sealing position (67) (see FIG. 1) clamps with sufficient sealing force between the cylinder inner wall (31) and the core wall (64).

The skirt (52), which extends along a ninth to a quarter of the piston length, for example, is a thin-walled ring that opens in a funnel shape in the unloaded state. The front outer edge

(53) of the skirt (52) encloses a cross-sectional surface area (55) which, according to FIG. 7, is greater than a cross-sectional surface area (63) whose circumference is defined by an imaginary contour line (62) lying at the foot of the skirt (52). The contour line (62) is shown in a partial view of the piston (10) in FIG. 7. The parking area (68) lies between the skirt (52) and the core wall (64).

Arranged on the rear face of the piston (50), there is a rear piston core (78), which likewise ends in a conical piston tip (79). Both piston tips (59, 79) have in each case a cone angle of 90 degrees, for example. Situated between the piston core (78) and the central portion (91) there is a shaft collar (72) whose diameter is exactly such that the sealing element (85) in the sealing position (87) (see FIG. 1) clamps with a sufficient sealing force between the inner wall (31) of the cylinder and the shaft collar (72). This diameter is greater than the diameter of the core wall (84). The width of the shaft collar corresponds approximately to the width of the sealing element (85).

A tetrafluoroethylene/hexafluoropropylene copolymer (FEP) is used as the material for the piston (50). This material has self-lubricating properties in conjunction with the aforementioned material of the cylinder (10), such that no separate lubricating agents are needed between the piston (50) and the cylinder (10). Alternative materials that can be chosen are, among others, perfluoroalkoxy copolymer (PFA), ethylene-tetrafluoroethylene (E TFE) or polyvinylidene fluoride (PVDF). Non-injectable polytetrafluoroethylene (PTFE), for example, has a high lubricating action.

If appropriate, it is also possible to use a combination of materials, in which the core area (59, 61, 79) of the piston (50) is made from a material of low elasticity, while the skirts (52, 72) are made from a highly elastic material.

The sealing elements (65, 85), at least according to FIGS. 1 to 7 for example, are simple O-rings, that is, they each have an individual circular cross section in the unloaded state. In the respective sealing position (67, 87), they are positioned between the piston (50) and the cylinder (10) such that they bear tightly on the walls of both structural parts (10, 50). They are each elastically deformed in the process. They then generally have a cross-sectional shape deviating from the circular surface.

According to FIGS. 1 and 5, the front O-ring (65) in the cylinder (10) bears on the inner wall (31) of the cylinder. It touches the piston (50) on the core wall (64) (see also FIG. 7) and on the inner edge (54) of the skirt. It is elastically flattened on the walls (31) and (64) because of the sealed clamping. The rear O-ring (85) sits clamped between the inner wall (31) of the cylinder and the shaft collar (72) (see FIG. 7). It is more strongly deformed here than the front O-ring.

The piston (50) is shown in motion in FIG. 3. The dynamic pressure developing in front of the piston (50) has forced the front O-ring (65) into the axial annular groove (57). In the process, the O-ring (65) has lost all contact with the inner wall (31) of the cylinder. Only the skirt (52) bears sealingly thereon. Directly after the start of the piston movement, the rear O-ring (85) is disengaged from the shaft collar (72) by the friction on the inner wall (31) of the cylinder. It now bears with slight residual clamping on the core wall (84). The rear O-ring (85) also has no contact with the inner wall (31) of the cylinder. For this reason, during the forward movement of the piston (50), the static sealing elements (65, 85) do not exert a braking action.

In FIG. 4, the front axial annular groove (57) has, in the illustrated plane of the drawing, another cross-sectional shape. The core wall (64) tapers from the front towards the rear, such that the O-ring (65), when pressed into the axial annular groove (57), has its mean diameter greatly reduced. The front piston portion (51) is for this purpose designed as a separate cap (49).

FIGS. 5 and 6 show alternative ways of mounting the rear O-ring (85) in place. In both cases, the O-ring (85) bears on a housing collar (46). According to the left-hand variant, the diameter of the radial wall (47) is chosen such that the O-ring (85) in its sealing position (87) bears on the wall (61) of the central piston portion (91). In the right-hand variant, the O-ring (85) bears half in the cylinder area and half in the piston area. In both cases, at the start of movement of the piston (50), the O-ring is pushed forcibly out of its sealing position into its parked position (see FIG. 6). It remains lying in the housing collar (46). It is thus in contact with the walls (47) and (48). It does not touch the core wall (84) of the piston (50).

FIG. 8 shows a front sealing element (105) in the form of a lip seal. The lip seal (105) is composed, for example, of a tubular portion (106) and a dish-shaped portion (107). The tubular portion (106) bears fixedly on the core wall (84). The dish-shaped portion (107) extends from the core wall (84) to the inner wall (31) of the cylinder. It also bears tightly on said inner wall (31) of the cylinder. In addition, with a piston (50) located in the rear piston position (99), it bears on the front edge of the skirt (52). If the piston (50) is moved forwards, the liquid to be ejected by the cylinder/piston unit presses the dish-shaped portion (107), with some areas deforming, behind the skirt (52). The outer edge of the portion (107) thus loses contact with the cylinder's inner wall (31).

Figure 9:
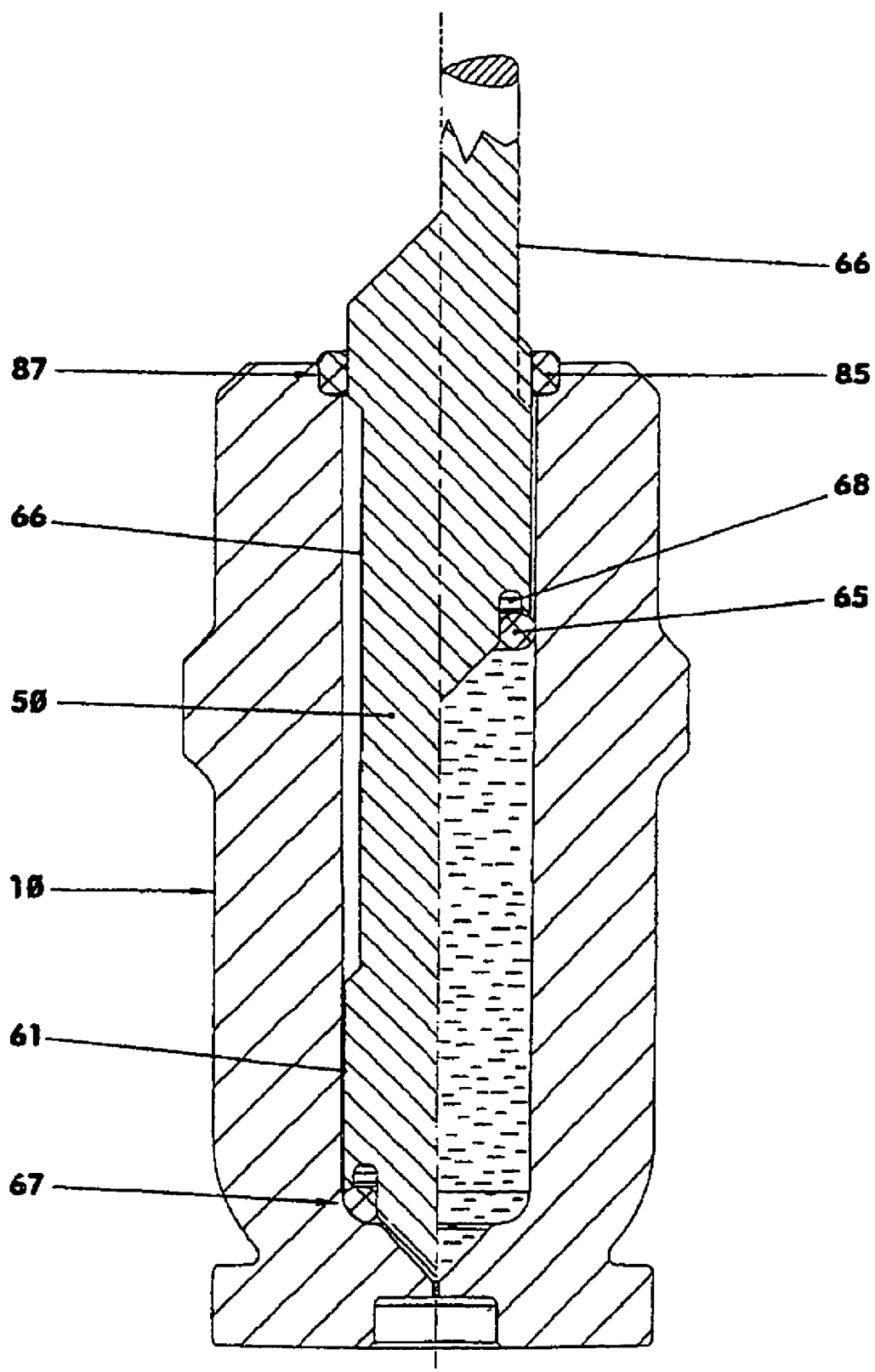
FIG. 9 shows a cylinder/piston unit with a long piston.

FIG. 9 shows a cylinder (10) in which a piston (50) is guided whose sealing positions (67) and (87) lie far apart from each other. The sealing positions (67) and (87) lie respectively in the front and rear end areas of the cylinder (10) (see left-hand side of piston in FIG. 9). The central piston wall area (61) has a waist (66) that extends within a certain area between the sealing positions (67, 87). The diameter of the waist (66) is chosen such that the rear sealing element (85), whose bearing conditions are explained in the description of FIG. 5, bears simultaneously on the piston (50) and on the cylinder (10) only in the two end positions shown in FIG. 9.

With this construction, an inserted piston (50) (see left-hand end of piston in FIG. 9) is also sealed off in a sterile manner relative to the cylinder (10). Such a cylinder/piston unit can be filled by the user just directly before use. For this purpose, the cylinder (10) is filled via the free jet aperture (39) and the nozzle bore (36), for example under hydraulic disengagement of the piston (50). As the piston (50) is pushed out hydraulically, for example with a filling syringe, the hydraulic pressure is low enough to ensure that the sealing element (65) is not pressed into the parking area (68).

Alternatively, the medicament to be administered can also be sucked into the cylinder. For this purpose, a suitable adapter is arranged on or integrally formed onto or into the end of the piston (50) directed away from the nozzle bore (36). The piston (50) can be withdrawn from the cylinder (10) via the adapter (not shown here).

When the piston (50) has reached its rear end position in the now filled cylinder (10), the sealing element (85) bears sealingly on the wall (61). If appropriate, the waist (66) can also be continued so far down (see broken line in FIG. 9, right-hand end of piston) that the sealing element (85) does not touch the piston (50) in this position, at least not in a sealing manner.

The cylinder/piston unit according to FIG. 9 can therefore be filled by the manufacturer or also by the end user. In both cases, the interior of the cylinder/piston unit, irrespective of whether it is empty or filled, is closed off in a sterile manner in the area of the piston (50).

The sealing elements (65, 85, 105) are made, for example, from silicone rubber, chlorinated rubber or butyl rubber. They are all closed rings. Their individual cross sections can be of any desired shape. If appropriate, the sealing elements (65, 85, 105) of a piston (50) each have different Shore hardnesses.

The following is a List of reference numbers:
1 active substance, filling
5 ram for piston drive
9 centre line
10 cylinder
11 front end, end with discharge element
12 end face, front
15 rear end
16 end face, rear
20 outer contour
21 adapter flange
30 chamber
31 inner wall of cylinder, inner contour
32 cylinder base
35 outflow funnel
36 nozzle bore, discharge element
39 free jet aperture
41 opening, front
42 bevel
45 opening, rear
46 housing collar
47 collar surface, radial
48 collar surface, axial
49 cap
50 piston
51 piston portion, front
52 skirt, elastic
53 outer edge of skirt, front
54 inner edge of skirt, front
55 cross section to outer edge
56 inner wall of skirt
57 axial annular groove
58 piston core, front
59 piston tip, front
61 piston wall, central
62 contour line, imaginary
63 cross section to contour line (62)
64 core wall, piston wall
65 sealing element, piston seal, O-ring
66 waist
67 sealing position
68 parking area
69 parked position
71 piston portion, rear
72 shaft collar
78 piston core, rear
79 piston tip, rear
84 core wall
85 sealing element, piston seal, O-ring
87 sealing position
88 parking area
89 parked position
91 piston portion, centre, central portion
98 piston position, between the end positions
99 piston position, rearward, rear end position
105 sealing element, piston seal, lip seal, front
106 tubular portion
107 dish-shaped portion

What is claimed is:

1. A cylinder/piston unit including a cylinder (10) and a piston (50) guided within the cylinder (10) and sealed off in a sterile manner by a rubber seal, the cylinder (10) and the piston (50) enclosing a chamber (30) that can be filled at least temporarily with active substance, and the cylinder (10) having at least one discharge element (36) at its front end (11), characterized in that;
the piston (50) having a resting rear position (99) sealed off relative to the cylinder (10) in a sterile manner by a static front sealing element (65, 105) and by a static rear sealing element (85), both the front sealing element (65, 105) and the rear sealing element (85) having respectively a sealing position (67, 87) where the front sealing element (65, 105) and the rear sealing element (85) each respectively bear on a wall (31, 47) of the cylinder (10) and the front sealing element (65, 105) and the rear sealing element (85) each respectively bear on a wall (64, 72) of the piston (50),
arranged spatially behind the front static sealing element (65, 105) and the rear static sealing element (85), the piston (50) having a parking area (68, 88) for receiving upon movement of the piston (50) the respective front sealing element (65, 105) and the rear sealing element (85), the parking area (68, 88) being unoccupied prior to the movement of the piston (50),
the piston (50) having an actuated state or position with the individual static front sealing element (65, 105) and the static rear sealing element (85) transferred from their respective sealing position (67, 87) into a parked position (69, 89) located in the parking area (68, 88), and each of the front sealing element (65, 105) and the rear sealing element (85) in the respective parked position (69, 89) touches only the cylinder wall (47, 48) or only the piston wall (64, 84),
at least one dynamic sealing element (52) is arranged on the piston side between the static sealing front sealing element (65, 105) and the static rear sealing element (85) and the at least one dynamic sealing element (52) bears on the inner wall (31) of the cylinder (10) at least when the piston (50) is actuated.

2. The cylinder/piston unit according to claim 1, characterized in that the dynamic sealing element (52) is a sealing lip in the form of a skirt (52).

3. The cylinder/piston unit according to claim 2, characterized in that the front static sealing element (65, 105) bears on the inner wall (56) of the skirt (52) when the piston (50) is actuated.

4. The cylinder/piston unit according to claim 2, characterized in that, when the piston (50) is actuated, the front outer edge (53) of the front skirt (52) expands to cover a cross-sectional surface area that corresponds to the cross-sectional surface area (55) of the inner wall (31) of the cylinder (10) covered by the contact line of the outer edge (53).

5. The cylinder/piston unit according to claim 2, characterized in that, the piston (50) between the skirt (52) and a piston core (58) has an axially extending annular groove (57), which is the parking area (68) for the front static seal (65, 105).

6. The cylinder/piston unit according to claim 1, characterized in that, the piston (50) in the resting rear position (99), the front static sealing element (65, 105) bears on the inner wall (31) of the cylinder (10), and the rear static sealing element (85) is in contact with a housing collar (46) of the cylinder (10), and the housing collar (46), in the area of radial contact by the rear sealing element (85), has a mean internal diameter that is greater than the mean internal diameter of the inner wall (31) of the cylinder (10).

7. The cylinder/piston unit according to claim 2, characterized in that, the skirt (52) comprises an elastic material.

8. The cylinder/piston unit according to claim 1, characterized in that, the static front sealing element (65) is an O-ring.

9. The cylinder/piston unit according to claim 1, characterized in that, the static rear sealing element (85) is an O-ring.

10. The cylinder/piston unit according to claim 1, characterized in that, the static front sealing element (105) is a lip seal.

11. The cylinder/piston unit according to claim 10, characterized in that, the static front sealing element (105) includes a tubular portion (106) and a dish-shaped portion (107), the tubular portion (106) of the front sealing element (105) bears fixedly on the piston core wall (84), the dish-shaped portion (107) in the resting rear position (99) extends from the piston core wall (84) to the inner wall (31) of the cylinder (10) while the dish-shaped portion simultaneously bears on the front outer edge (53) of the skirt (52).

* * * * *